United States Patent
Zhang et al.

(10) Patent No.: US 10,209,214 B2
(45) Date of Patent: Feb. 19, 2019

(54) BIOSENSOR

(71) Applicant: LEADWAY (HK) LIMITED, Hong Kong (CN)

(72) Inventors: Ziyi Zhang, Zhejiang (CN); Huanxi Ge, Zhejiang (CN)

(73) Assignee: LEADWAY (HK) LIMITED, Hong Kong (CN)

(*) Notice: Subject to any disclaimer, the term of this patent is extended or adjusted under 35 U.S.C. 154(b) by 74 days.

(21) Appl. No.: 14/775,688

(22) PCT Filed: Nov. 22, 2013

(86) PCT No.: PCT/CN2013/087660
§ 371 (c)(1),
(2) Date: Mar. 22, 2016

(87) PCT Pub. No.: WO2014/153969
PCT Pub. Date: Oct. 2, 2014

(65) Prior Publication Data
US 2016/0195490 A1 Jul. 7, 2016

(30) Foreign Application Priority Data

Mar. 28, 2013 (CN) .......................... 2013 1 0106521

(51) Int. Cl.
*G01N 27/327* (2006.01)
*G01N 33/543* (2006.01)

(52) U.S. Cl.
CPC ..... *G01N 27/3272* (2013.01); *G01N 33/5438* (2013.01)

(58) Field of Classification Search
CPC .......................... G01N 27/327; G01N 27/3272
See application file for complete search history.

(56) References Cited

U.S. PATENT DOCUMENTS 6,471,839 B1 10/2002 Yamamoto et al.
6,613,205 B1 9/2003 Steiner et al.
(Continued)

FOREIGN PATENT DOCUMENTS

CN 2791894 Y * 6/2006 .............. H01M 4/86
CN 1922478 A 2/2007
(Continued)

OTHER PUBLICATIONS

English language translation of CN 2791894 Y obtained from the EPO website on Aug. 3, 2017.*

(Continued)

*Primary Examiner* — Alexander S Noguerola
(74) *Attorney, Agent, or Firm* — Acuity Law Group, P.C.; Michael A. Whittaker

(57) ABSTRACT

A biosensor comprising an insulative substrate (1) and an electrode system arranged on the insulative substrate (1). The electrode system comprises thereon a reagent capable of reacting with a test sample. The electrode system comprises functional electrodes (2, 3, and 4) used for testing and assisted diffusion electrodes (12) used for controlling the diffusion of the reagent. The functional electrodes (2, 3, and 4) are arranged between the assisted diffusion electrodes (12). Because the assisted diffusion electrode (12) are capable of overcoming the effect of surface tension of the insulative base board, the reagent is allowed to diffuse smoothly and uniformly on the electrode system and to arrive at a predetermined position.

7 Claims, 12 Drawing Sheets

(56) References Cited

U.S. PATENT DOCUMENTS

| | | | |
|---|---|---|---|
| 7,316,766 | B2 | 1/2008 | Chen et al. |
| 7,429,865 | B2 | 9/2008 | Dreibholz et al. |
| 7,648,617 | B2 | 1/2010 | Miyazaki et al. |
| 7,655,119 | B2 | 2/2010 | Davies |
| 8,940,138 | B2 * | 1/2015 | Fujiwara ............ G01N 27/3274 204/228.6 |
| 2005/0109618 | A1 | 5/2005 | Davies |
| 2005/0136500 | A1 | 6/2005 | Yang et al. |
| 2005/0265897 | A1 | 12/2005 | Maruo et al. |
| 2006/0070878 | A1 | 4/2006 | Wu et al. |
| 2007/0227911 | A1 * | 10/2007 | Wang ................. A61B 5/14532 205/792 |
| 2008/0110768 | A1 | 5/2008 | Bae et al. |
| 2009/0145756 | A1 | 6/2009 | Zhu et al. |
| 2011/0042211 | A1 | 2/2011 | Huang et al. |
| 2011/0297557 | A1 * | 12/2011 | Wu ..................... G01N 27/3274 205/792 |
| 2012/0298528 | A1 | 11/2012 | Asano et al. |
| 2013/0062221 | A1 | 3/2013 | Cai et al. |

FOREIGN PATENT DOCUMENTS

| | | | |
|---|---|---|---|
| CN | 100533136 | C | 8/2009 |
| CN | 201497726 | U | 6/2010 |
| CN | 101900701 | A | 12/2010 |
| CN | 1846131 | B | 1/2012 |
| EP | 0636879 | A2 | 2/1995 |
| EP | 1548427 | A1 | 6/2005 |
| EP | 1816479 | A1 | 8/2007 |
| EP | 1927851 | A2 | 6/2008 |
| JP | H07110313 | A | 4/1995 |
| JP | H1134462 | A | 2/1999 |
| JP | 2005043122 | A | 2/2005 |
| JP | 2007256069 | A | 10/2007 |
| WO | 2004017057 | A1 | 2/2004 |
| WO | 2005083412 | A1 | 9/2005 |
| WO | 2007108388 | A1 | 9/2007 |
| WO | 2009056299 | A1 | 5/2009 |

OTHER PUBLICATIONS

EPO computer-generated Englsih language translation of CN 2791894 Y. Downloaded Nov. 27, 2017.*

International Search Report issued by SIPO in PCT/CN2013/087660 dated Mar. 6, 2014—incl Engl lang transl.

Office Action issued by SIPO in Chinese Patent Application No. 201310106521.0 dated Nov. 2, 2017—incl machine generated Engl lang transl.

Office Action issued by SIPO in Chinese Patent Application No. 201310106521.0 dated Apr. 3, 2018—incl machine generated Engl lang trans.

Wang et al., Electrochemical Properties of Ionic Liquid on Porous Carbon Electrode. Chem Res. Jun. 2005;16 (2):38-41- incl machine generated Engl lang transl.

Zhang, Electrochemical testing technology. In Electrochemical Series: Electrochemical Testing Techniques(Chinese Edition). Chemical Industry Press Pub. Date :Sep. 1, 2010—incl machine generated English translation (55 pages total).

Zhang, Preparation and properties of coal-based activated carbon electrode materials. in Coal-based Activated Carbon Electrode Material Preparation and Properties(Chinese Edition). Coal Industry Pub. Date :Sep. 1, 2009 version 1—incl machine generated English translation (16 pages total).

* cited by examiner

BIOSENSOR

FIELD OF THE INVENTION

The present invention involves a biosensor used for determining concentration of physical signs.

BACKGROUND OF THE INVENTION

In recent years, from the original detection by clinical laboratory samples to the rapid detection realized in the doctor's office or point of care test, the field of medical health detection has been changed dramatically. A disposable biosensor with electrode system has been frequently used in rapid detection. Taking daily glucose detection of a diabetic as an example, nowadays, the glucose level of a diabetic can be immediately known by using a disposable biosensor at the diabetic's home, and it will help the diabetic to know his/her own physical condition, thereby adjusting his/her dietary structure, or going to the hospital and asking the doctor to adjust his/her dosage of medication according to his/her daily monitoring data. Hence, the accuracy of this type of disposable biosensor is very important in the daily monitoring of diseases.

This type of biosensor with electrode system can be used in the detection of various kinds of substances. Depending on different analytes, reaction reagents added to the electrode system are also different. Taking the biosensor used for determining glucose level of blood as an example, at first, the reaction reagents such as glucose oxidase are added to a working electrode. When a blood sample is dropped to the working electrode, since the enzyme reaction reagent dissolves in blood, glucose in the blood will react with the oxidase on the working electrode, and then electron acceptor will be reduced. After the enzyme reaction finishes, the reduced electron acceptor will be electrochemically oxidized and the concentration of glucose in the sample can be obtained by calculating the current value of oxidation.

The basic structure of this type of biosensors includes an insulative substrate, on which there's an electrode system which at least contains a working electrode and a counter electrode, and at least one working electrode is covered by reaction reagents that produce detectable signals according to concentration of determined substance in the sample; and a channel for detecting sample is formed by separating layer, the channel is on the working electrode and the counter electrode. When the sample to be detected goes through the channel, it reacts with the reaction reagent in the channel thereby producing detectable signals. An instrument reads the testing results according to the signals.

The amount of reaction reagent in the channel for detecting the sample reaction has a great influence on the test result. Therefore, how to precisely control the amount of reaction reagents that acts in the reaction has been a big technical problem in this field. The amount of reaction reagents that acts in the reaction is equal to the product of area of sample channel and the thickness of reaction reagent layer, therefore, it is a major problem that shall be solved to accurately control both sizes of sample channels among different products produced at the same batch and the uniformity of thickness of reaction reagent.

To accurately control the sizes of sample channels can be obtained by improving the accuracy of moulds and selecting proper materials, however, it is a relatively difficult technical problem to control the uniformity of the thickness of the reaction reagents.

As shown in FIG. 1 of the U.S. Pat. No. 7,655,119, an electrode comprising an insulative substrate 16 that have a rectangle reagent-diffusion control zone 18, the electrode that needs reaction reagents and exposed by the rectangle reagent-diffusion control zone is rightly the active zone of the electrode. The reaction reagents have been dropped onto the control zone 18 and contact with the electrode, and other parts of the electrode that have not acted in the reaction will not be dropped by the reaction reagents since they are covered by the insulating plate 16, hence, the reaction reagents will be limited in the required area on the working electrode. We found that, the dropped reagents often can not fully cover the whole rectangle zone by dropping reaction reagents, for example, the reagents can not reach the four vertex angles of the rectangle reagent-diffusion control zone. It means that the products produced at the same batch have different reaction reagent-covered areas. Once the volumes of dropped reaction reagents are equal, the thicknesses of reaction reagents of the products produced at the same batch have deviations, so, the amount of the reaction reagents that act in the reaction would not be equal. The results obtained will be inaccurate by using the product for testing. When using this manner of dropping reaction reagents onto the electrodes, more serious undesirable phenomena occur. The reaction reagents can not fully cover the whole rectangle zone, and even part of reagents overflows the both sides of the rectangle reagent diffusion-control zone.

When testing the sample with the biosensor, usually, a very small amount of sample, for example, only 0.5 microliter to 1 microliter of liquid, is required. Biosensor has also been made into a very tiny structure, and the reaction reagents covered at the electrodes are even smaller. In the research of improving the accuracy of testing, people hardly notice that the diffusion of reaction reagent is various in such a small area of electrode and notice the effect on the testing results brought by the variety. People have always studied to improve the detection accuracy of biosensor from aspects of structure of electrode, material of electrode, testing methods and meters. However, we found that when applying rectangle reagent diffusion control zone to control the distribution of reaction reagents at the electrode, the area of rectangle control zone is very small. And the reagent will form a hemispheric drop in the groove of the rectangle control zone because of surface tension, which causes the uneven of reagent thickness at the electrode to form a result of thick center and thin edge, especially, at the edge of coatings area, it would be uneven, or the reaction reagents would concentrate on the center of electrode active region. The edge surface tension of hemispheric drop prevents the further diffusion around, which causes reagent blanks between reagent edge and four vertex angles, which means those four vertex angles can not be filled up with by reaction reagents. Some the active region of the electrode of biosensors produced in this way may be evenly filled up with by the reaction reagent, while some vertex angles in the active region of the electrode have no reaction reagents or the covered thickness are not uniform. The lack of reaction reagent at some parts of the electrode will cause that some samples fail in acting in the reaction, and the unevenness of thickness of the reaction reagents covered at the electrode will make the changes of reaction rate which does not conform the pre-established method, which will lead to the inaccuracy of testing results.

And just as in the China Patent 200480023924.8, method of adding reagent by insulating plate-covering has not been used, it uses seam coating to directly make reaction reagent coated on the electrode to create continuous strips. Because the reagent area of coating is very large, it even contains some parts that do not need the addition of reaction reagent. It will lead to the waste of reagent and increase product cost. On the other hand, due to the surface tension on the insulative substrate, the diffusion of the reagent has been suffered from certain resistance that hampers the even diffusion of reaction reagent in the electrode system, which makes the reaction reagent can not reach the pre-established sites.

Since the size of biosensor that is used to detect the glucose concentration of human's blood is very tiny, and the detection mechanism is also very complex, moreover, the applied blood sample amount is often between 0.3 and 1.0 micrometer, therefore, present technical level can only bring a relatively accurate detection result. According to the statutory requirements of biosensor that is used to detect the glucose concentration of human blood from U.S. FDA: as long as the positive or negative deviation of over 95% of detection result and standard glucose concentration is within 20%, the product is considered as a qualified one. It can be seen that it is very difficult technically to improve the detection accuracy of the glucose concentration of human blood by biosensor.

According to the statistic data of International Diabetes Federation (IDF) in 2011, diabetes patients in the worldwide have been increased to 366 million at present, and this number is expected to reach nearly 600 million within 20 years. In China, the prevalence rate of diabetes has been increased by nearly two times within 10 years. In 2010, the prevalence rate of Chinese adult diabetes was 9.7%, and diabetes patients have been reached to more than 140,000,000. Due to the huge cardinal number, even if the testing accuracy rate can be increased by 1%, then, in the world, 3.6 million person-time will be avoid of being misdiagnosed, so there will be 3.6 million people benefit from that, which would bring considerable economic and social interests.

It is reminded by medical specialists that diabetes is an important part of non-infectious diseases. Lacking of reasonable monitor and treatment, the long-term hyperglycemia of diabetes patients may lead to damages of multisystem in the body and cause various acute and chronic complications, such as cardiovascular disease, diabetic nephropathy, diabetic neurogenic lesion and diabetic retinopathy lesion and so on. Therefore, the accuracy of testing is very important, for it can effectively make sure that both patients and doctors notice the changes of illness and revise the pharmacy dosage and eating habits as soon as possible, so as to prevent the patients from being a state of hyperglycemia and from horrible complication. Whether the reaction reagents have been correctly distributed at the electrode is a key factor that has always been ignored by people while ensures the accuracy of the whole testing results.

BRIEF SUMMARY OF THE INVENTION

In order to overcome the above-mentioned defects, one of purposes of the present invention is to provide a biosensor with precise positioning and low amount of reaction reagents, A biosensor comprising an insulative substrate and an electrode system on the insulative substrate, the electrode system includes a reaction reagent that can react with samples to be detected and an insulating layer thereon; the electrode system is partially covered by the insulating layer, but forms a closed region without any insulating layer covered, the reaction reagent lies on the closed region, the reaction reagent lies on a part of the electrode which is in the closed region; the closed region formed by the insulating layer has a non-sharp-angled closed boundary; and the reaction reagent covers the closed region, and it does not extend beyond the closed boundary.

As further improvement of the present invention, the shape of the closed boundary is either a circle, an oval, two relative ovals, or rectangle with four circular vertex angles.

As further improvement of the present invention, the reaction reagent exactly fills the closed region, and the area covered by the reaction reagent is equal to the area of the closed region.

As further improvement of the present invention, the thickness of the insulating layer is 1-50 micrometers.

As further improvement of the present invention, the thickness of the insulating layer is 3-30 micrometers.

As further improvement of the present invention, the material of the insulating layer is hydrophobic material.

As further improvement of the present invention, the electrode system comprises an assisted diffusion electrode at each of the two sides of the electrodes, covered by the reaction reagent, in the electrode system, and the assisted diffusion electrodes stand side by side with the electrodes covered by the detection reagent.

The second purpose of the present invention is to provide a method of manufacturing a biosensor, comprising:
1) forming an electrode system on an insulative substrate;
2) forming an insulating layer on the electrode system, the insulating layer covers parts of the electrode system and forms a closed region without any insulating layer thereon, and the closed region has a closed boundary without any sharp angles;
3) adding a reaction reagent to the closed region, so that the reaction reagent fills the closed region, but it does not extend beyond the closed boundary of the closed region;
4) drying the reaction reagent.

As further improvement of the present invention, the closed boundaries of the closed region selected from a circle, an oval or a square body with four circular vertex angles.

As further improvement of the present invention, the thickness of the insulating layer is 3-30 micrometers.

The third purpose of the present invention is to provide a biosensor, comprising an insulative substrate and an electrode system on the insulative substrate, wherein the electrode system comprises a reaction reagent that can react with samples to be detected thereon, wherein the electrode system includes functional electrodes for detection and assisted diffusion electrodes for controlling the diffusion of the reaction reagent, and the functional electrodes are located between the assisted diffusion electrodes.

As further improvement of the present invention, it comprises at least two assisted diffusion electrodes.

As further improvement of the present invention, at least two assisted diffusion electrodes are respectively located at the outsides of the functional electrode.

As further improvement of the present invention, the distance between the assisted diffusion electrodes and the functional electrodes is precisely so that the front end of the reaction reagent added to the functional electrode can touch the assisted diffusion electrode.

As further improvement of the present invention, the functional electrodes comprises a working electrode, a counter electrode and a reference electrode, and the functional electrodes are arranged in parallel with the assisted diffusion electrode, and are roughly parallel to each other.

As further improvement of the present invention, there are two assisted diffusion electrodes, which is located in the outer side of the functional electrode.

As further improvement of the present invention, it comprising an insulating layer which covers part of the electrode system, the insulating layer forms a closed region without an insulating layer at the location of the reaction reagent, the reaction reagent locates on the electrode in the closed region, the closed region has a non-sharp-angled closed boundary surrounded by the insulating layer, and the reaction reagent covers the closed region, it does not extend beyond the closed boundary.

As further improvement of the present invention, the shape of the closed boundary selected from a circle, an oval, two relative ovals, or a rectangle with four circular vertex angles.

As further improvement of the present invention, the thickness of the insulating layer is 3-30 micrometers.

Advances of the present invention include: according to a large number of experiments show that, because of the application of sample-adding pattern in non-sharp-angled reagent diffusion control zone, the biosensor described in the present invention has effectively overcome the edge effect of the reaction reagent, which makes reaction reagent evenly distribute at corresponding regions of the electrode, so that it can accurately control the uniformity of reaction reagent thicknesses of biosensors produced at the same batch so as to improve the accuracy of testing results. During the process of manufacturing biosensor, the added reaction reagent fills with the addition zone of reaction reagent that has the same shape with it, which avoids the phenomenon that those four vertex angles added by reaction reagent have not been filled up with by reaction reagent. On the other hand, the described manufacturing method of the present invention is simple, so there is no need to control the dosage of reaction reagent without any complicated steps. Moreover, there are at least two assisted diffusion electrodes in the electrode system of the biosensor of the present invention, this assisted diffusion electrode is able to overcome the surface tension of the insulative substrate, which makes the reagents can smoothly and evenly distribute in the electrode system and arrive their pre-established places. Besides, the reaction reagents will not overflow the pre-established region.

BRIEF DESCRIPTION OF THE DRAWINGS

FIG. 4 is the microscopic photos of the electrode showed FIG. 1 after the reaction reagent added on;

FIG. 6 is the microscopic photos of the electrode showed FIG. 5. after the reaction reagent added on;

FIG. 8 is the microscopic photos of the electrode showed FIG. 7 after the reaction reagent added on;

FIG. 10 is the microscopic photos of the electrode showed FIG. 9 after the reaction reagent added on;

FIG. 12 is the microscopic photos of the electrode showed FIG. 11 after the reaction reagent added on;

FIG. 14 is the microscopic photos of the electrode showed FIG. 13 after the reaction reagent added on;

DETAILED DESCRIPTION OF THE INVENTION

The present invention is described in detail as follows with the combination of the drawings. The preferred embodiments are only finitely listed without departing from the spirit of the invention, and other specific embodiments generated when persons skilled in the art combine the prior art with the invention are not excluded.

Figure 1:
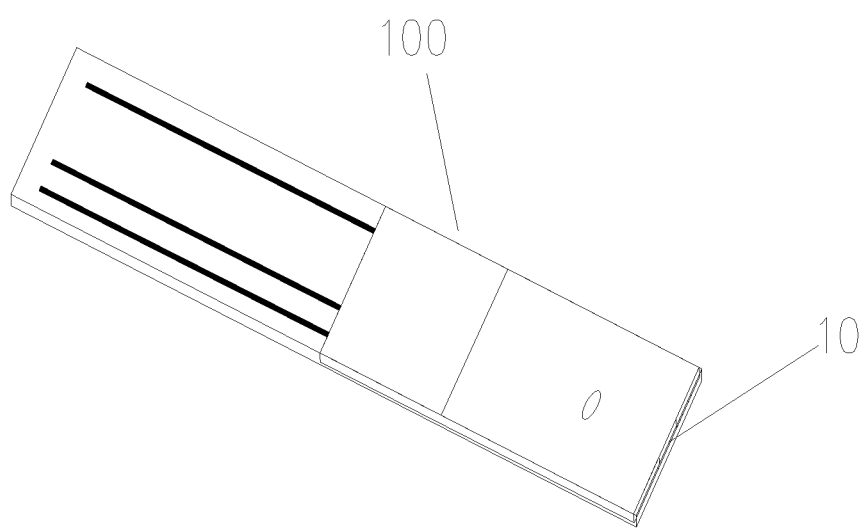
FIG. 1 is the first biosensor of the present invention.
Figure 2:
FIG. 2A-2E are the manufacturing processes of the biosensor as showed in FIG. 1.
Figure 2:
Figure 2:
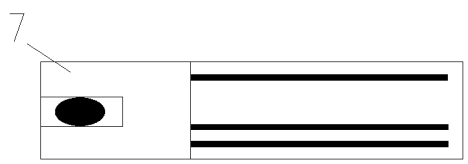
Figure 2:
Figure 2:
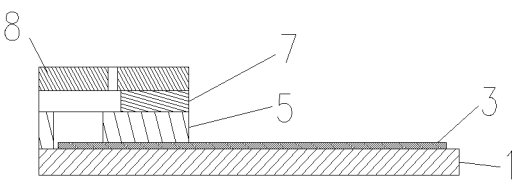
Figure 3:
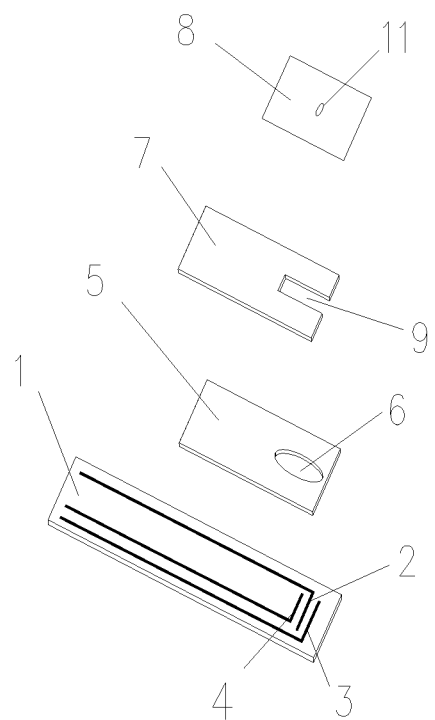
FIG. 3 is the breakdown drawing of the biosensor showed in FIG. 1.

As shown in FIG. 1 to FIG. 3, the biosensor 100 consists of an insulative substrate 1 and an electrode system on the insulative substrate. The electrode system includes working electrode 2, counter electrode 3 and reference electrode 4. The reagent diffusion control layer 5 covers certain areas of the electrode system, and the control layer 5 includes a reagent diffusion control zone 6 which has an opening. The reagent diffusion control layer 5 is insulating material, hence, it is also called as insulating layer, i.e. the reagent diffusion control layer is equal to insulating layer in this patent application. The opening area of the reagent diffusion control zone 6 is equal to the area of the reagent which is added on the electrode, and the opening is precisely located on the active region of the electrode. The active region of the electrode refers to the part of electrodes having the reaction reagent and can transmit electronic signals. In the embodiment showed in FIG. 3, a gap layer 7 with a groove is on the reagent diffusion control layer 5, an upper cover 8 covers the gap layer 7 and forms a sample channel 10 used to add sample. There is also a gas vent 11 in the upper cover 8, when the sample flows through the channel by capillary action, the gas at the front of the sample is ejected through the gas vent 11, which ensures a smooth flow of sample in the channel.

In another way to explain, the biosensor of the present invention consists of an insulative substrate 1 and an electrode system on the insulative substrate. The electrode system comprising an insulating layer 5 and the reaction reagent that reacts with the test sample. The insulating layer 5 covers part of electrode system, while it has formed a closed region 6 without any insulating layer at the place of the reaction reagent. (This closed region is equal to the reagent diffusion control zone 6), the reaction reagent stands on the electrodes of the closed region 6, the closed region surrounded by the insulating layer has a non-sharp-angled closed boundary. The reaction reagent covers the closed region, but it does not go beyond the closed boundary. The shapes of the closed boundary may be a circle, an oval, two relative ovals, or four rectangles with its vertex angles of circular arcs. In one preferred embodiment, the reaction reagent exactly fills the closed region, and the coverage area of reaction reagent is equal to the area of the closed region. The thickness of the insulating layer is 1-50 micrometers. It would be better that the thickness of the insulating layer is 3-30 micrometers. The material of the insulating layer is hydrophobic material. As a further improvement of the present invention, at both sides of electrodes covered by detection reagent in the electrode system, there is an assisted diffusion electrode at each side, and the assisted diffusion electrode stands side by side with the electrodes covered by detection reagent.

The above embodiment is usually called as parallel capillary sample-adding technology. In another embodiment method, the vertical sample-adding technology can be utilized, that is, the upper cover with a sample-adding hole adheres to the control layer 5, and the sample-adding hole of the upper cover precisely stands at the reagent diffusion control zone, and its area is equal to or a little smaller than the opening area of this control zone. That is, when the sample is added to the sample-adding hole, the sample vertical mobility contacts and reacts with the reagent in the control zone.

The reagent diffusion control zone 6 is a hole without any sharp angles, and the added reaction reagent diffuses is in the control zone and it is able to reach all of pre-established regions in the control zone. The shapes of the reagent diffusion control zone may be a hole with a circular arc, such as a circle, an oval, a calabash and so on. The shapes can also be other shapes without any sharp angles, such as a quadrangle with its four circular-arc vertex angles within the diffusion control zone. Through a large amount of experiments, we are surprised to find that employing the reagent diffusion control zone of the present invention, when the reaction reagent has been added to the electrode, it can form a reagent layer with even diffusion and uniform thickness, and the reagent layer fills up with the whole active region of the electrode.

Both depth and area of the reagent diffusion control zone 6 shall be confirmed according to the amount of actual needs. In an embodiment, the depth of the reagent diffusion control zone is 1-50 micrometers, the depth of 3-30 micrometers is better, and the depth of 5-20 micrometers is the best.

When the upper cover 8 covers the gap layer 7, it with the groove-shape of gap layer 7 forms a sample-adding channel 10. In order to make samples smoothly flow through the channel and finally arrive in the electrode system, there is also an air hole 11 of the sample-adding channel 10 for the upper cover 8.

FIG. 2 is a method of the biosensor in the embodiment of FIG. 3 in the present invention. However, the manufacturing method described in the present invention is not limited to those steps showed in FIG. 2.

As show in FIG. 2A, there is the insulative substrate 1 and the electrode system on the insulative substrate. The electrode system described in this embodiment includes a working electrode 2, a counter electrode 3 and a reference electrode 4. In another embodiment, the electrode system includes a working electrode 2, a counter electrode 3 and a reference electrode 4, and it also comprising an assisted diffusion electrode 12 showed in FIG. 7.

The insulative substrate 1 can use but it is not limited to the following insulation materials: carbon, polystyrene, polycarbonate, polyvinyl chloride resin and polyester and so on. In a specific embodiment, the substrate is made up of polyethylene glycol terephthalate (PET). The thickness of the substrate is 3-10 mils, for example, 5 mils (mil, milli-inch, a distance unit, 1 mil is equal to one thousandth of inch, that is 0.0254 millimeter.) PET strip can provide proper support, and it is also suitable to 14 mils PET albuginea. Of course, many different thicknesses can also play a very excellent function in the present invention. The insulative substrate provides supports for both electrode and electrode wire.

In another way to explain, the method of manufacturing a biosensor in the present invention includes following steps:

1) forming an electrode system on the insulative substrate;
2) forming an insulating layer on the electrode system, the insulating layer covers part of electrode system and forms a closed region without the insulating layer, and this closed region has a closed boundary without any sharp angles;
3) adding reaction reagent to the closed region so that the reaction reagent can cover the closed region, the reaction reagent should not go beyond the closed boundary of the closed region;
4) drying the reaction reagent.

The various ways can be used to put electrode on the insulative substrate 1. These ways include but not just be limited to screen printing, ink-jet printing, binding agent bonding, lithographic plate printing, laser carving and so on. Silver or silver chloride, graphite, palladium, gold, platinum, iridium stainless steel and other suitable electric-conduction materials can be used as the material of electrode. The electrode can be made up of these materials together, instead of single material. For example, the electrode that contacts with the contact end of the detection instrument is made of silver material.

As shown in FIG. 2B, when the electrode system has been dried and formed into a shape on the insulative substrate 1, the reagent diffusion control layer 5 is placed on the electrode system, and the reagent diffusion control zone 6 in the control layer perfectly stands on the active region of the electrode system. The reaction reagent 200 has been added to the reagent diffusion control zone 6, and it evenly diffuses in the active region of the electrode, moreover, the reagent area that actually covers in the electrode is equal to the pre-established region.

By various ways, the reagent diffusion control layer 5 has been placed in the electrode system, such as bonding, heat-sealing, ultrasonic welding or grinding and so on. The reagent diffusion control layer 5 comes from hydrophobic materials, such as insulating polyphenyl ethylene, insulating hydrophobic ink or glue. The glue may be double faced adhesive tape, single faced adhesive tape or transferred adhesive tape and so on. In one embodiment, the reagent diffusion control layer 5 is a double faced adhesive tape, one side of the double faced adhesive tape can make the control layer adhered to the substrate with an electrode system, another side of the double faced adhesive tape, the upper cover 8 may be adhered to the gap layer 7.

The reaction reagent contains one or more chemical components which are used to detect the existence or concentration of the analyte in the liquid sample. For example, the reaction reagents of electrochemical biosensor consist of oxidordeuctase and mediator, they are used to detect samples, producing a reaction product that can be detected by electronic detection system. In the embodiment of detecting the glucose concentration in the blood, the reaction reagents include glucose oxidase, hexaammine ruthenium (III) chloride, BSA, CaSO4, TritonX-100 and PVP and so on. The reaction reagents have been added to the electrode through various techniques, such as screen printing, liquid dropping adding, knife coating, spraying of groove nozzle and so on.

Figure 17:
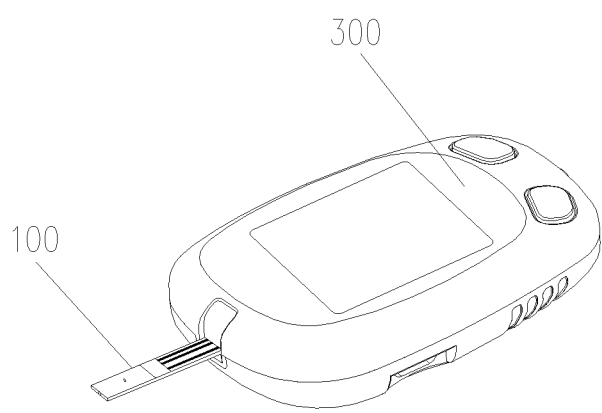
FIG. 17 is a state diagram of the combined use of the biosensor and detector instrument.

As shown in FIG. 2C, when the reaction reagents added to the electrode have been dried, the gap layer 7 with the groove 9 will be put on the substrate that is equipped with an electrode system and reaction reagents. In the end with the reaction reagent layer, gap layer covers the electrode that does not contact with samples, and the reaction reagent is exposed in the groove 9. The gap layer dose not cover the electrode which is opposite end of the electrode with the reaction reagent layer, the exposed electrode can touch the pin of a detecting instrument 300, just as the connection method that is showed in FIG. 17. By various ways, the gap layer has been placed on the electrode system, such as bonding, heat-sealing, ultrasonic welding or grinding and so on. Its material is insulating hydrophobic material, such as the material of binding agent. When the gap layer is insulating polystyrene, both sides of the manufacturing-layer can be coated with binding agent to adhere to reagent diffusion control layer 5 and upper cover 8. In one embodiment method, in order to make samples smoothly flow in the groove, the groove 9 can be made a hydrophilic treatment, for example, the surface of the groove is coated surfactant or carried out plasma treatment, making the surface of the groove contacted with samples full of hyprophilia.

As shown in FIG. 2D, the upper cover 8 places on the gap layer 7 to produce biosensor. As shown in FIG. 2E, after the upper cover 8 has been placed on the gap layer with the groove, it makes the groove 9 become a channel 10 for the sample to enter into the biosensor. The sample enters into the biosensor through an inlet, it enters into successfully utilizing the capillary function formed by groove and contact the reaction reagent. The material of upper cover selected from an insulating hydrophobic material or other kinds of materials. The upper cover 8 has the gas vent 11, the gas vent 11 is located on the groove 9 and far away from the entry end of the sample inlet.

Figure 7:
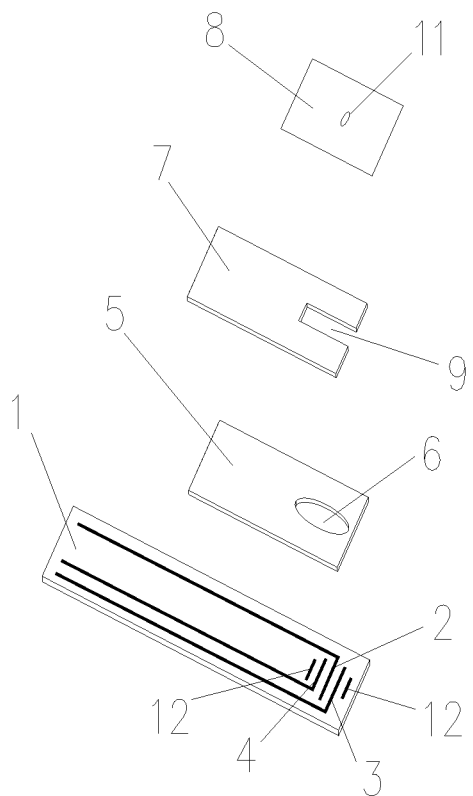
FIG. 7 is the breakdown drawing of the biosensor with an assisted diffusion electrode.

Another biosensor 100 described in the invention as shown in FIG. 7, comprising an insulative substrate 1 and an electrode system on the insulative substrate. The electrode system includes functional electrodes, such as a working electrode 2, a counter electrode 3 and a reference electrode 4. The electrode system also comprising the assisted diffusion electrode 12 on the insulative substrate, and the assisted diffusion electrode can assist the reaction reagent added on the functional electrodes quickly and evenly diffuse in the electrode. Both sides of the electrode system that needs the addition of reaction reagent have the assisted diffusion electrode. For example, the functional electrode is located between assisted diffusion electrodes, and the assisted diffusion electrodes are located at the outside of functional electrode separately. The distance between the assisted diffusion electrodes and the functional electrodes is proper, and this distance makes the front end of reaction reagent dropping added at the functional electrodes can touch the assisted diffusion electrodes.

In preferred embodiment, the assisted diffusion electrodes are made up of porous materials, such as carbon electrode. Through studying, inventors of this patent find that the porous structure of the electrode material will form capillary effect, so that the solution of reached the electrode quickly diffuses in the assisted electrodes under the function of capillary effect. This power produced by the diffusion in the assisted diffusion electrodes is stronger than the surface tension of liquid, the solution can quickly diffuse in the electrodes and arrive the pre-established scale. Therefore, when the reaction reagent diffusions and it's shape is an ova, an approximate oval, an approximate rectangle or the size of its one side is greater than the other side, and when we are going to set up an diffusion electrode in a place that is further than the center of the shape after the diffusion of reaction reagent (for example, the outside of two ellipse axial ends and the outside of shorter edges of rectangle), the diffusion speed of the reagent from this direction will be quicker than that of speed without setting up diffusion electrode, hence, it is beneficial for the reagent to arrive the outline boundary from various directions at the same time, so that it is favorable to improve the evenness of reagent diffusion. In order to achieve this goal, we can set up one or more assisted diffusion electrodes that are used to increase the diffusion speed of reagent at any place where the diffusion speed of reagent is relatively slow. In another preferred embodiment, the assisted diffusion electrode will be made a hydrophilic treating in advance in accord with the nature of adding solution.

In the embodiment as shown in FIG. 7, the biosensor also comprising a reaction reagent diffusion control layer 5 covered the electrode system, and the control layer 5 comprising a the reagent diffusion control zone 6 which comprising an opening. The area of opening in the reagent diffusion control zone 6 is the same as the area of reagent added on the electrode, and it is precisely located on the active region of the electrode. The gap layer 7 comprising the groove 9 is on the reaction reagent diffusion control layer 5, the upper cover 8 covers the gap layer 7 and forms a sample channel 10 used to add samples with the groove 9 of gap layer 7. The upper cover 8 comprising a gas vent, when the sample flows through the channel by capillary action, the gas at the front of the sample is ejected through the gas vent 11, which ensures the sample flows in the channel successfully.

The reagent diffusion control zone 6 is a hole without any sharp angles, and the added reaction reagent diffuses in the control zone, and it is able to reach all of pre-established regions in the control zone. The shapes of the reagent diffusion control zone may be a hole with a circular arc, such as a circle, an oval, a calabash and so on. The shapes can also be other shapes without any sharp angles, such as a quadrangle with its four circular-arc vertex angles within the diffusion control zone.

The biosensor showed in FIG. 7 is manufactured utilizing the method showed in FIG. 2. During the process of manufacture, when/after/before adding the electrode system showed in FIG. 2A, the assisted diffusion electrode 12 is installed on the insulative substrate.

In another way to explain, the biosensor in the present invention consists of an insulative substrate 1 and an electrode system on the insulative substrate. The electrode system comprises a reaction reagent that can react with the sample. The electrode system comprising functional electrodes that are used for detection (2, 3, 4) and an assisted diffusion electrode that are used to control the diffusion of reaction reagents (10, 12), and the functional electrode is located between the assisted diffusion electrodes. In the present invention, the biosensor comprises at least two assisted diffusion electrodes. The two assisted diffusion electrodes are located at the outside of the functional electrode separately. The distance between the assisted diffusion electrodes and the functional electrodes perfectly makes the front end of the reaction reagent added at the functional electrodes can touch the assisted diffusion electrodes. The functional electrodes comprising a working electrode, a counter electrode and a reference electrode, and all of these functional electrodes stand side by side with the assisted electrodes, and almost parallel. The biosensor comprising two assisted diffusion electrodes located at the outside of the functional electrode separately. It comprises an insulating layer that covers a part of the electrode system. The insulating layer has formed a closed region without any insulating layer at the place of the reaction reagent, the reaction reagent is on the closed region of the electrode. The closed region surrounded by the insulating layer has a non-sharp-angled closed boundary. The reaction reagent covers the closed region, and it does not go beyond the closed boundary. The shapes of the closed boundary may be a circle, an oval, two relative ovals, or four rectangles with its vertex angles of circular arcs. The thickness of the insulating layer is 3-30 micrometers.

The following content will explain the working principles of the present invention.

Figure 18:
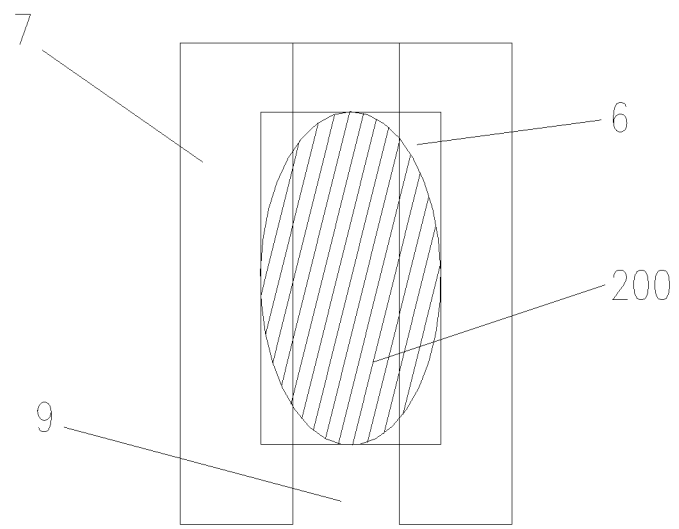
FIG. 18 is schematic diagram of detecting the diffusion of reagents in the prior art.

Refer to FIG. 18. It is one of phenomenon about the diffusion of reagents in the prior art. Therein, sign 200 is the reaction reagent after diffused, sign 6 is a closed region surrounded by insulating materials (it is also called as the reagent diffusion control zone in this application), sign 7 is a gap layer, sign 9 is a groove formed by the gap layer 7, and the gap layer 7 is used to form a sample channel 10, the sample channel 10 is formed by the side wall of the groove 9, the insulative substrate 1 and the upper cover 8. After research and experiments, we find that those reaction reagents which outsides the channel 10 (for example, the reagents that covered by the gap layer) almost do not react with the samples. Only those reaction reagents in the channel 10 can react with the samples, the quantity of the reaction reagents in the channel 10 is an important factor for the detection results. Therefore, it would be beneficial to improve the accuracy of detection results of these products to effectively reduce the deviation of the reaction reagent quantity within the channels among various products produced at the same batch.

In prior art, since the closed region 6 formed by the insulating layer (it is also called as the reagent diffusion control zone in this application) is square, rectangle and other sharp-angled shapes. When different products produced at the same batch are added with reaction reagents, the shapes of reaction reagents after diffusion in the closed region 6 are very different (because the reaction reagent is not easy to cover all of sharp-angled regions). There existed great difference in the area of different products after the reaction reagent diffused, however, total amount of the reaction reagent is almost same. Therefore, the thickness of the reaction reagent after reagent diffusion in different products exist great difference, it cause the amount of the reaction reagent in the channel 10 has a big difference. That is, amount of the reaction reagents in the channel 10 are poor consistency. It will lead to rather different detecting results for various products produced at the same batch to detect the same samples, so as to an inaccuracy of detecting results.

Figure 19:
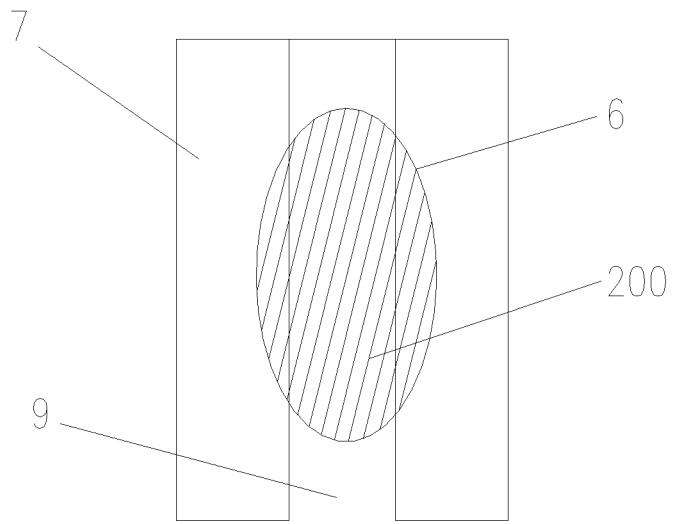
FIG. 19 is schematic diagram of detecting the diffusion of reagents in the present invention.

Please refer to FIG. 19. In the present invention, since the closed region 6 (it is also called as the reagent diffusion control zone in this application) formed by insulating layer is square, rectangle and other sharp-angled shapes. When liquid reaction reagents are added, it is easier for the reaction reagents to fills all of the closed region 6 than the prior art, it is not easy to leave some "dead angles" that are not covered by the reaction reagents. Therefore, when different products of the same batch are added with reaction reagents, the shapes of reaction reagents after diffusion in the closed region 6 are less differences (they are basically in line with the sharps in the closed regions). Among different products, they are hardly different in their areas after the diffusion of reaction reagents (they are basically in line with the areas of the closed regions), and the total amount of the added reaction reagents are equal, so the thicknesses of reaction reagents among different products are almost equal after the diffusion, and the amount of reaction reagents in the channel 10 is basically equal. That is, among different products, the quantities of the reaction reagents within the channel 10 are good consistency. It will lead to hardly different detecting results for various products produced at the same batch to detect the same samples so as to improve the accuracy of detecting results.

In the embodiment of adding the assisted electrodes in the present invention, the research and experimental results showed that: Adding assisted electrodes in the regions where the reaction reagent is hard to arrive (including the regions that the reaction often or occasionally can not arrive within a pre-established time) or the regions where the reagent is obviously later to arrive than other regions (this region shall be covered by the reaction reagents) will improve the diffusion ability of these reaction reagents in these regions. Therefore, it is beneficial to promote the even diffusion of reaction reagents within the closed region and to cover the whole closed region, while they will not go beyond the boundary of this closed region, so as to achieve the goal of even thicknesses of reaction reagents after the diffusion. In this patent application (it includes but it is not limited to the specification book or right claims), the reaction reagent fills, fills up with, properly fills, properly fills up with, covers, properly covers (or other similar terminology) the closed region 6. It means that the reaction reagent has basically covered the whole area of the closed region 6, but it is fundamentally not beyond or exceeded the boundary of the closed region 6. According to above analysis, this technology improves the accuracy of test results.

Embodiment 1: Reaction Reagent Adds to Electrodes Utilizing Oval Reagent Diffusion Control Zone As showed in FIG. 3, the biosensor comprising an insulative substrate 1, a working electrode 2, a counter electrode 3 and a reference electrode 4. The reaction reagent diffusion control layer 5 covers on the electrode system, and the control layer 5 comprising an elliptic the reagent diffusion control zone 6. The area of the opening of the reagent diffusion control zone 6 is equal to the area of the electrode which needs to be added the reaction reagent, and it is precisely located on the active region of the electrode. The biosensor also comprising a gap layer 7 and an upper cover 8 with a gas vent.

Figure 4:
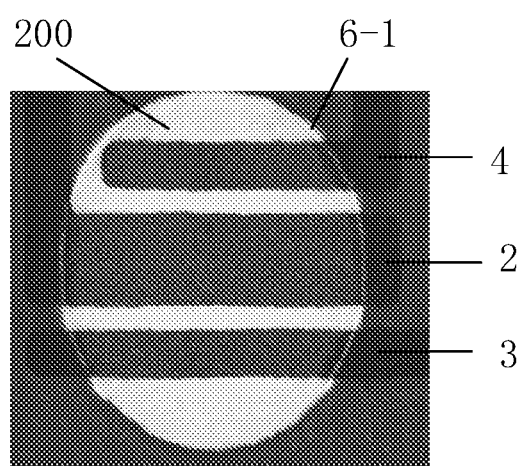

During the process of manufacturing biosensor, the reaction reagents have been added to the electrodes through the oval reagent control zone by spot-dropping. After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 4, the reaction reagents added to the electrodes diffuse evenly without any exceeding outside the refined boundary of reagent diffusion control zone sideline 6-1. Moreover, the reaction reagent 200 covered the whole reaction reagent zone established by sideline 6-1, and the whole control zone reflects the color of the reaction reagent. Therefore, in the biosensor in this embodiment, the reaction reagents have a good uniformity in electrodes.

Figure 5:
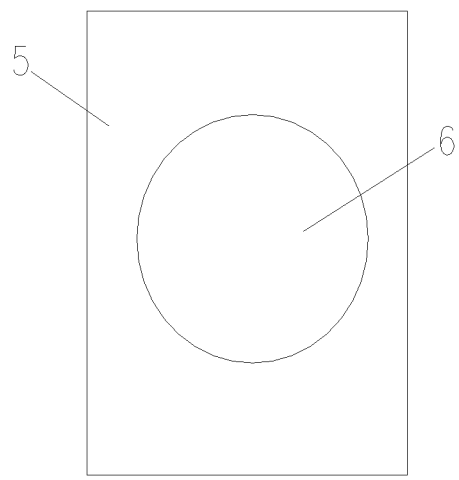
FIG. 5 is structure diagram of the second kinds of reagent diffusion control layer.

Embodiment 2: Reaction Reagent Adds to Electrodes Utilizing a Rounded Reagent Diffusion Control Zone As showed in FIG. 5, the reagent diffusion control layer 5 comprising a rounded reagent diffusion control zone 6.

Figure 6:
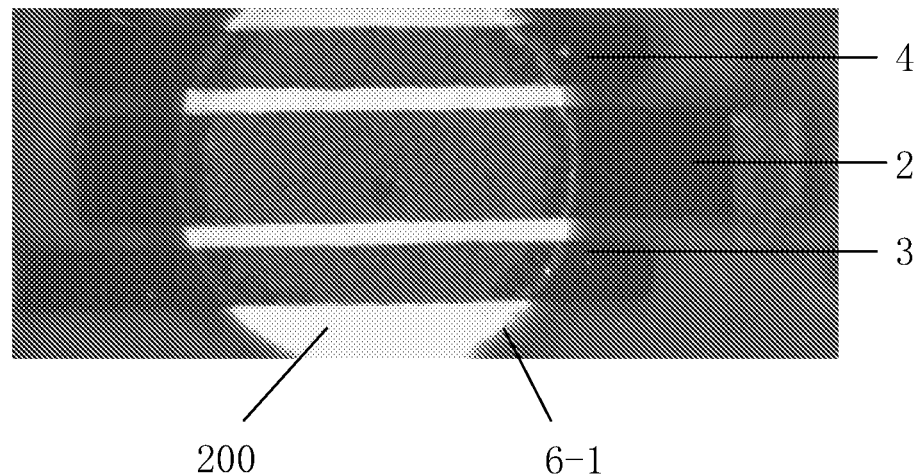

During the process of manufacturing biosensor, the reaction reagents have been added to the electrodes through the oval reagent control zone by spot-dropping. After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 6, the added reaction reagents evenly diffuse in the working electrode 2, the counter electrode 3 and the reference electrodes without any exceeding outside the refined boundary of reagent diffusion control zone sideline 6-1. Moreover, reaction reagent 200 covered the whole reagent zone, that is, the whole control zone reflects the color of reaction reagent. Therefore, in the biosensor in this embodiment, the reaction reagents have a good uniformity in electrodes.

Figure 8:
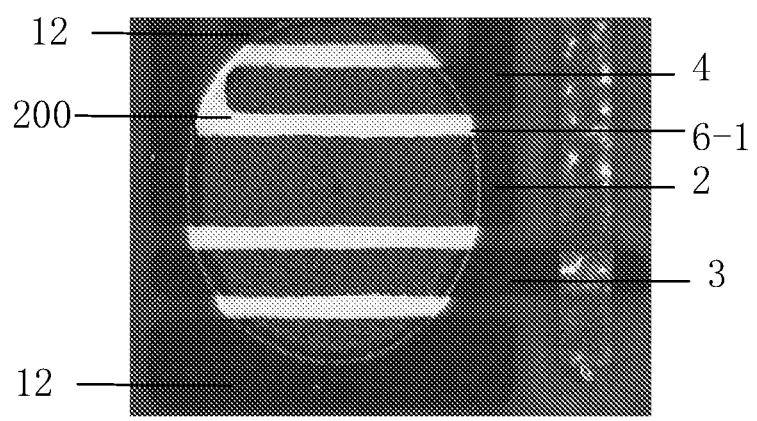

Embodiment 3: Reaction Reagent Adds to the Electrode System with an Assisted Diffusion Electrode As showed in FIG. 7, the electrode system of the biosensor comprising functional electrodes 2, 3, 4 and an assisted electrode 12. The biosensor also comprises a control layer of the reaction reagent diffusion 5 with an oval regent diffusion control zone 6. During the process of manufacturing biosensor, the reaction reagents have been added to the electrodes through the oval reagent control zone by spot-dropping. After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 8, the added reaction reagents diffuse evenly in the electrodes without any exceeding outside the refined boundary 6-1 of reagent diffusion control zone. Moreover, reaction reagent 200 coved the whole reagent zone, that is, the whole control zone reflects the color of reaction reagent. Therefore, in the biosensor in this embodiment, the reaction reagents have a good uniformity in the electrodes.

Figure 9:
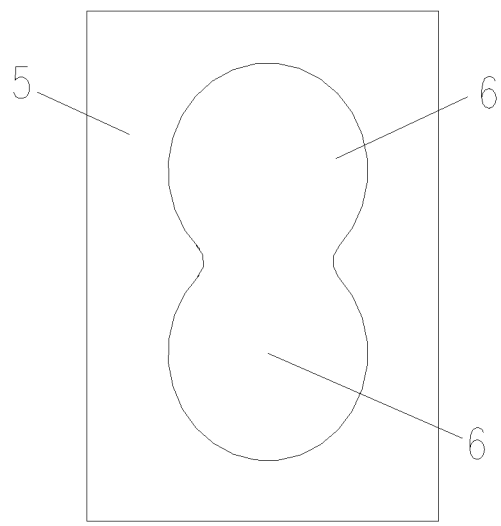
FIG. 9 is structure diagram of the third kinds of reagent diffusion control layer.

Embodiment 4: The Design Utilizes a Double-Circular Reagent Diffusion Control Zone Combined and an Assisted Diffusion Electrode As showed in FIG. 9, it is a reagent diffusion control layer 5 with an double-oval reagent diffusion control zone 6. End-to-end double-oval reagent diffusion control layer can be used to manufacture two biosensors at the same time. During the process of manufacturing biosensor, two sets of electrode systems are placed on the insulative substrate by end-to-end, the electrode system comprising a working electrode 2, a counter electrode 3 and a reference electrode 4, and it also comprising an assisted diffusion electrode 12. In FIG. 9, there are three assisted diffusion electrodes 12, two of them lie the outside of two sets of functional electrodes (a working electrode 2, a counter electrode 3 and a reference electrode 4), and the other is in the middle of the two sets of functional electrodes as a commonly-used assisted diffusion electrode. In FIG. 9, after the reaction reagent diffusion-layer has been placed on the electrode system, the reaction reagents are added on the electrode system.

Figure 10:
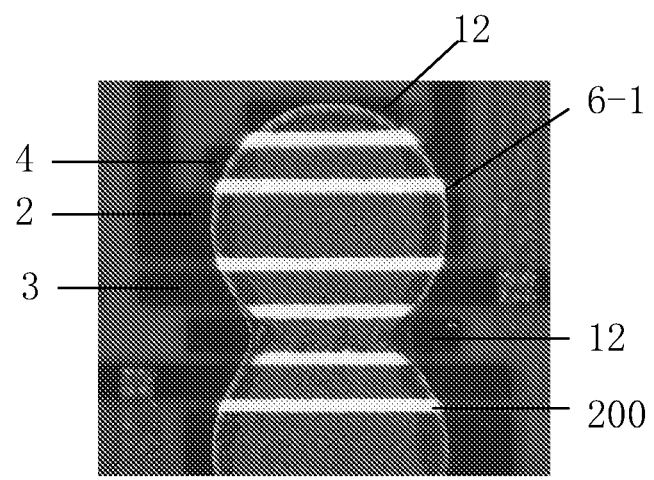

During the process of manufacturing biosensor, the reaction reagents have been added to the electrodes through the oval reagent control zone by spot-dropping. After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 10, the reaction reagents added to the electrodes diffuse evenly without any exceeding outside the refined boundary 6-1 of reagent diffusion control zone. Moreover, the reaction reagent 200 covered the whole reagent zone, that is, the whole control zone reflects the color of reaction reagent. Therefore, the reaction reagents have a good uniformity in the electrodes of this embodiment.

Figure 11:
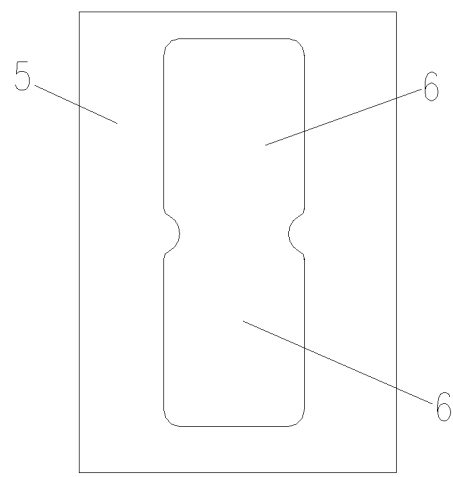
FIG. 11 is structure diagram of the fourth kinds of reagent diffusion control layer.

Embodiment 5: The Design Utilizes a Double-Rectangle Reagent Diffusion Control Zone with Around Vertex Angles and an Assisted Diffusion Electrode As showed in FIG. 11, it is a reagent diffusion control layer 5 with an double-rectangle 6. The double-rectangle reagent diffusion control layer can be used to manufacture two biosensors at the same time. During the process of manufacturing biosensor, two sets of electrode systems are placed on the insulative substrate by end-to-end, the electrode system comprising a working electrode 2, a counter electrode 3 and a reference electrode 4, and it also comprising an assisted diffusion electrode 12. In FIG. 11, there are three assisted diffusion electrodes 12, two of them lie the outside of two sets of functional electrodes (a working electrode 2, a counter electrode 3 and a reference electrode 4), and the other is in the middle of the two sets of functional electrodes as a commonly-used assisted diffusion electrode. In FIG. 9, after the reaction reagent diffusion-layer has been placed on the electrode system, the reaction reagents are added on the electrode system.

Figure 12:
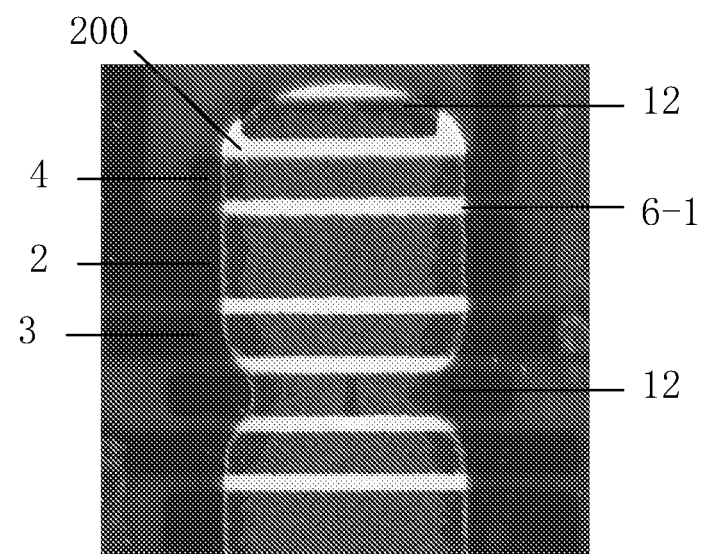

During the process of manufacturing biosensor, the reaction reagents have been added to the electrodes through the oval reagent control zone by spot-dropping. After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 12, the reaction reagents added to the electrodes diffuse evenly without any exceeding outside the refined boundary 6-1 of reagent diffusion control zone. Moreover, the reaction reagent 200 covered the whole reagent zone, that is, the whole control zone reflects the color of reaction reagent. Therefore, the reaction reagents have a good uniformity in the electrodes of this embodiment.

Figure 13:
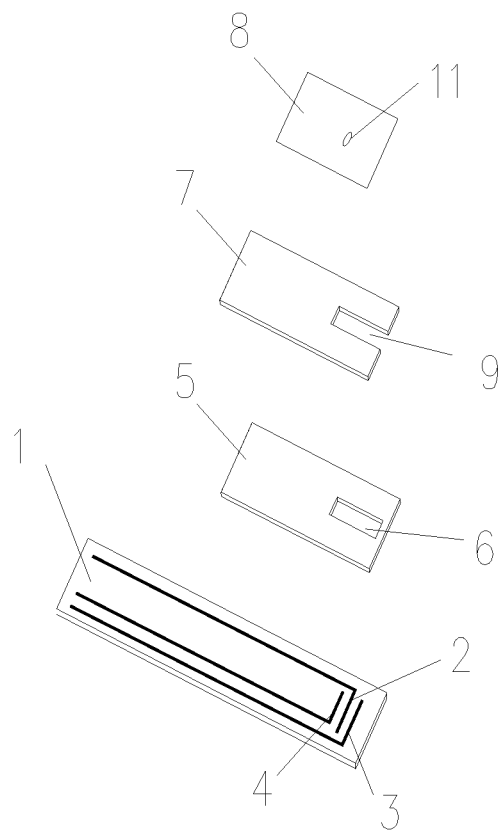
FIG. 13 is the breakdown drawing of the biosensor of the prior art.

Embodiment 6: Reaction Reagent Adds to the Electrode System Utilized a Right-Angle Rectangle Reagent Diffusion Control Zone As showed in FIG. 13, the biosensor is manufactured as described in the prior art. The insulative substrate 1 has been added to the electrode system, and the diffusion control layer 5 with rectangle reagent diffusion control zone 6 covers the electrode system, and the rectangle reagent diffusion control zone lies on the active region of the electrode system, that means the region is the region of the electrode which needs to be added reaction reagent. The reaction reagents have been added to the electrodes through the groove hole in the reagent diffusion control zone by spot-dropping method, and then the gap layer 7 and the upper cover 8 are coved.

Figure 14:
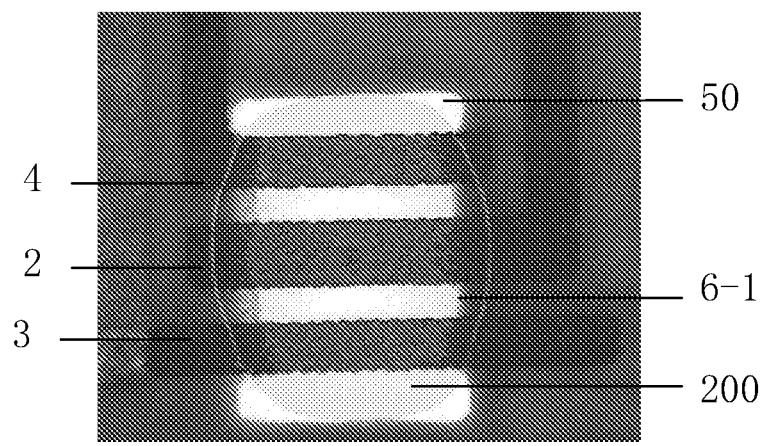
Figure 16:
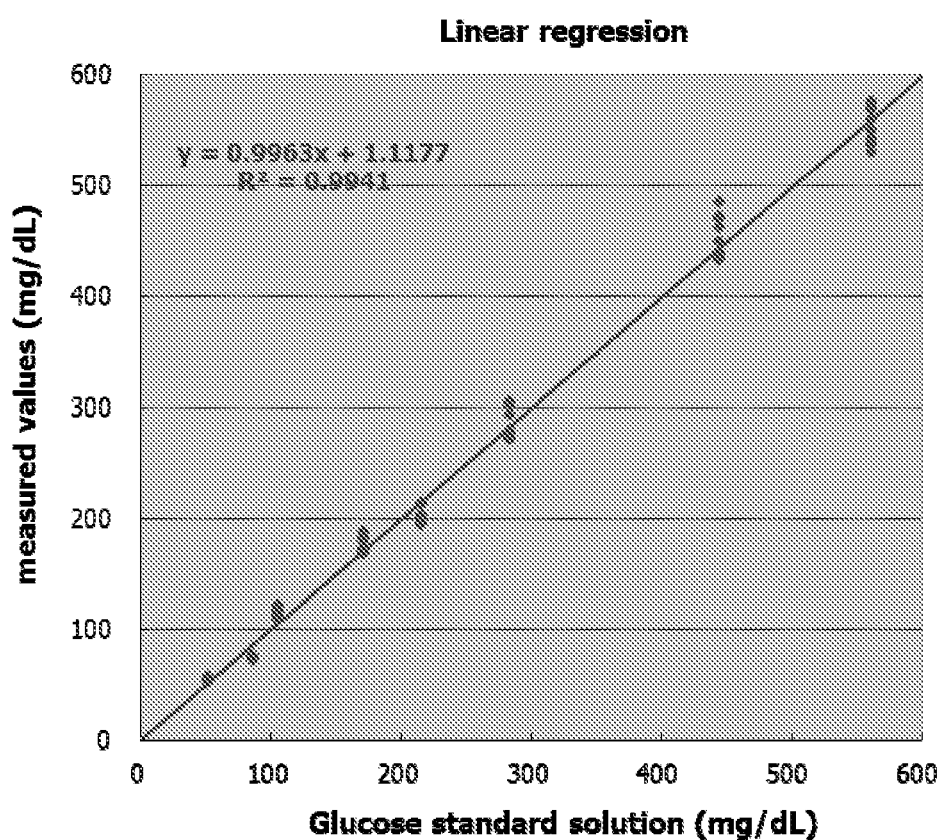
FIG. 16 is a linear graph of glucose standard solution detected by the biosensor of the prior art.

After the reaction reagents have been added to the electrode system, using digital microscope (Type of microscope MOTICAM 2306, Manufacturer, MOTIC China Group Co., Ltd) to take photos to the distribution of reagents in the electrodes so as to observe the distribution of reagents in the electrodes. As showed in FIG. 14, The added reaction reagents can not cover the whole rectangle zone, and there is no reagent in the four angles 50 in the rectangle diffusion control zone, and the added reagent overflows both sides of the rectangle zone, which causes the non-uniformity of reagent thickness in the electrode.

detected correlation coefficient $R^2$ has reached to 0.9993. Glucose concentrations in standard are detected by the biosensors of the prior art in embodiment 6 depicted in Table 2 and FIG. 16. In embodiment 6, the biosensor does not include an assisted diffusion electrode, reagent diffusion control zone of the biosensor is a rectangle with an orthogonal vertex angle. The test results show that the detected correlation coefficient $R^2$ has just reached to 0.9941.

TABLE 1

Test results of the glucose concentrations in standard by the biosensors in embodiment 3

| Testing result | Preparation concentration of glucose (mg/dL) | | | | | | | |
|---|---|---|---|---|---|---|---|---|
| (mg/dL) | 55.7 | 84.0 | 117.9 | 177.9 | 223.5 | 298.0 | 448.7 | 575.0 |
| Testing 1 | 57 | 82 | 116 | 177 | 223 | 298 | 449 | 565 |
| Testing 2 | 55 | 84 | 118 | 178 | 226 | 294 | 454 | 582 |
| Testing 3 | 55 | 81 | 120 | 177 | 223 | 293 | 441 | 582 |
| Testing 4 | 56 | 80 | 122 | 180 | 218 | 293 | 448 | 566 |
| Testing 5 | 56 | 82 | 119 | 175 | 222 | 295 | 439 | 577 |
| Testing 6 | 56 | 83 | 119 | 183 | 229 | 295 | 449 | 563 |
| Testing 7 | 57 | 82 | 122 | 179 | 224 | 303 | 458 | 566 |
| Testing 8 | 56 | 82 | 119 | 178 | 224 | 294 | 459 | 565 |
| Testing 9 | 57 | 84 | 121 | 175 | 223 | 309 | 455 | 581 |
| Testing 10 | 57 | 84 | 120 | 174 | 226 | 296 | 449 | 585 |
| Average value | 56.2 | 82.4 | 119.6 | 177.6 | 223.8 | 297.0 | 450.1 | 573.2 |
| SD | 0.8 | 1.3 | 1.8 | 2.7 | 2.9 | 5.2 | 6.6 | 8.9 |
| CV | 1.4% | 1.6% | 1.5% | 1.5% | 1.3% | 1.7% | 1.5% | 1.6% |

TABLE 2

Test results of the glucose concentrations in standard by the biosensors in embodiment 7

| Testing concentration | Preparation concentration of glucose (mg/dL) | | | | | | | |
|---|---|---|---|---|---|---|---|---|
| (mg/dL) | 51.5 | 86.0 | 105.4 | 170.6 | 215.2 | 283.2 | 444.4 | 560.9 |
| Testing 1 | 57 | 74 | 122 | 173 | 195 | 276 | 470 | 543 |
| Testing 2 | 57 | 73 | 112 | 188 | 204 | 272 | 472 | 540 |
| Testing 3 | 58 | 74 | 109 | 183 | 197 | 279 | 462 | 560 |
| Testing 4 | 57 | 77 | 121 | 183 | 196 | 302 | 435 | 537 |
| Testing 5 | 55 | 73 | 115 | 170 | 214 | 280 | 485 | 531 |
| Testing 6 | 54 | 75 | 122 | 180 | 215 | 279 | 440 | 577 |
| Testing 7 | 54 | 75 | 117 | 172 | 203 | 305 | 433 | 551 |
| Testing 8 | 54 | 76 | 111 | 184 | 203 | 294 | 436 | 576 |
| Testing 9 | 56 | 77 | 119 | 169 | 214 | 274 | 439 | 569 |
| Testing 10 | 55 | 77 | 110 | 173 | 196 | 274 | 449 | 571 |
| Average value | 55.7 | 75.1 | 115.8 | 177.5 | 203.7 | 283.5 | 452.1 | 555.5 |
| SD | 1.5 | 1.6 | 5.1 | 6.8 | 8.0 | 12.2 | 18.7 | 17.3 |
| CV | 2.7% | 2.1% | 4.4% | 3.8% | 3.9% | 4.3% | 4.1% | 3.1% |

Embodiment 7: Accuracy Analysis of the Measurement of the Glucose Concentration in Standard by a Biosensor Preparing glucose standard solution, and using the biosensor in embodiment 3 and embodiment 6 to detecting the glucose concentration in standard solution.

Figure 15:
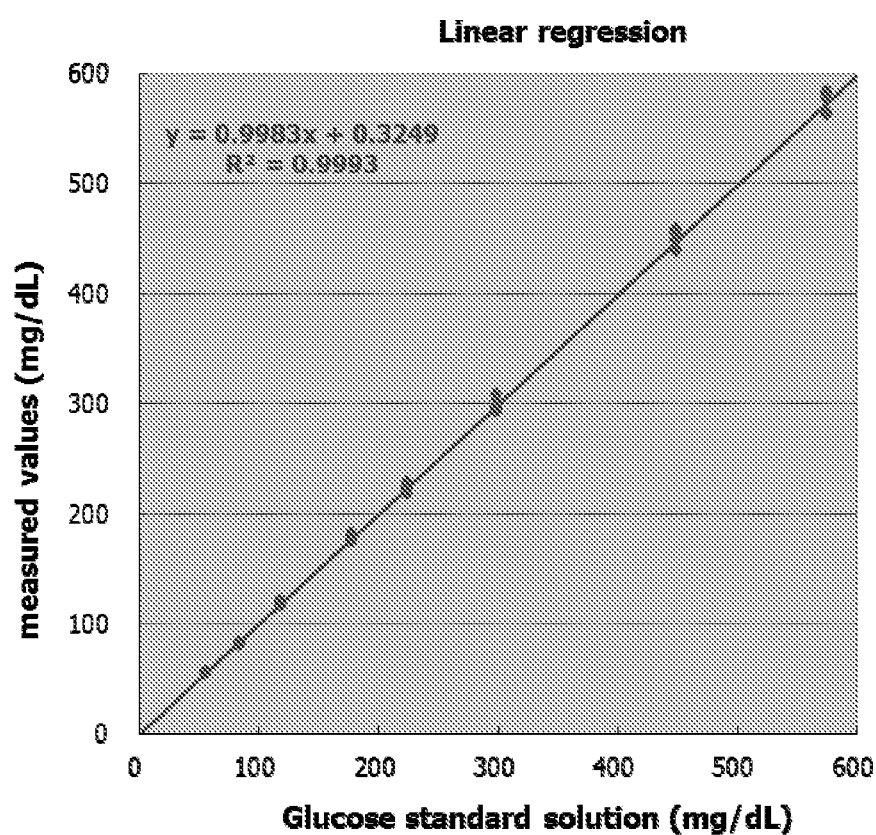
FIG. 15 is a linear graph of glucose standard solution detected by the biosensor of the present invention.

Glucose concentrations in standard are detected by the biosensor of embodiment 3 of the present invention depicted in Table 1 and FIG. 15. In embodiment 3, the electrode system of the biosensor includes an assisted diffusion electrode and reagent diffusion control layer with an oval reagent diffusion control zone. The test results show that the It is clear from the experimental results that the biosensors with an assisted diffusion electrode and reagent diffusion control layer with an oval reagent diffusion control zone are used in embodiment 3. Both coefficient of variation (CV) and standard deviation (SD) of the testing results are lower than the variable coefficient (CV) and standard deviation (SD) of the testing results of the biosensors (i.e., no assisted diffusion electrode and rectangle reagent diffusion control zone) in the prior art. Therefore, the glucose concentration of sample is tested by the biosensors of the present invention, and its concentration test has a good reproducibility (i.e., when many biosensors produced at the same batch are used to test samples at the same batch, the differentiation among the testing results are less than the one in the prior art) and testing results are more accurate.

What is claimed is:

1. A biosensor, comprising:
an insulative substrate and an electrode system on the insulative substrate,
wherein the electrode system comprises a reaction reagent that can react with samples to be detected thereon, functional electrodes for detection, and assisted diffusion electrodes for controlling the diffusion of the reaction reagent, wherein the functional electrodes are located between the assisted diffusion electrodes, and
an insulating layer that covers part of the electrode system, the insulating layer having a hole forming a closed region, wherein the reaction reagent is located in the closed region on the electrode system, the closed region is surrounded by the insulating layer and comprises a closed boundary without any sharp angle, and the reaction reagent covering the closed region without extending beyond the closed boundary.

2. The biosensor of claim 1, wherein there are at least two assisted diffusion electrodes.

3. The biosensor of claim 2, wherein the at least two assisted diffusion electrodes are respectively located at the outsides of the functional electrodes.

4. The biosensor of claim 1, wherein the functional electrodes comprise a working electrode, a counter electrode and a reference electrode, and the functional electrodes are arranged in parallel with the assisted diffusion electrodes, and are generally parallel to each other.

5. The biosensor of claim 4, wherein there are two assisted diffusion electrodes, and the functional electrodes are located between the two assisted diffusion electrodes.

6. The biosensor of claim 1, wherein the shape of the closed boundary is selected from the group consisting of a circle, an oval, two relative ovals, or a rectangle with four circular vertex angles.

7. The biosensor of claim 6, wherein the thickness of the insulating layer is from 3-30 micrometers.

* * * * *